(12) United States Patent
Bailly et al.

(10) Patent No.: US 11,291,536 B2
(45) Date of Patent: *Apr. 5, 2022

(54) WHALE CONCEPT-FOLDING MESH FOR TIPP PROCEDURE FOR INGUINAL HERNIA

(71) Applicant: Sofradim Production, Trévoux (FR)

(72) Inventors: Pierre Bailly, Caluire-et-Cuire (FR); Mylene Desorme, Villeurbanne (FR); Genevieve Doucet, Villefrancehe sur Saone (FR)

(73) Assignee: SOFRADIM PRODUCTION, Trevoux (FR)

( * ) Notice: Subject to any disclaimer, the term of this patent is extended or adjusted under 35 U.S.C. 154(b) by 253 days.

This patent is subject to a terminal disclaimer.

(21) Appl. No.: 16/423,566

(22) Filed: May 28, 2019

(65) Prior Publication Data
US 2019/0274808 A1 Sep. 12, 2019

Related U.S. Application Data

(63) Continuation of application No. 14/860,748, filed on Sep. 22, 2015, now Pat. No. 10,327,882.

(30) Foreign Application Priority Data

Sep. 29, 2014 (EP) ..................... 14306522

(51) Int. Cl.
*A61F 2/00* (2006.01)
(52) U.S. Cl.
CPC .... *A61F 2/0063* (2013.01); *A61F 2002/0072* (2013.01); *A61F 2230/0008* (2013.01);
(Continued)

(58) Field of Classification Search
CPC .. A61F 2/0063; A61F 2/02; A61F 2/00; A61F 2/2436; A61F 2002/0072;
(Continued)

(56) References Cited

U.S. PATENT DOCUMENTS 1,187,158 A 6/1916 Mcginley
3,118,294 A 1/1964 Laethem
(Continued)

FOREIGN PATENT DOCUMENTS

CA 1317836 C 5/1993
DE 19544162 C1 4/1997
(Continued)

OTHER PUBLICATIONS

Amid, P., "Lichtenstein tension-free hernioplasty: Its inception, evolution, and principles," Hernia, 2004; pp. 1-7, 8, published online Sep. 2003.
(Continued)

*Primary Examiner* — Jocelin C Tanner
(74) *Attorney, Agent, or Firm* — Weber Rosselli & Cannon LLP

(57) ABSTRACT

The present invention relates to a device (1) for introducing a flexible prosthesis into a surgical incision, comprising a globally tubular body (2) having a proximal end (2*a*) and a distal end (2*b*), said tubular body being designed for receiving the prosthesis in a folded configuration in a sliding way, wherein the tubular body is provided with an open longitudinal slit (3) extending from said proximal end (2*a*) to said distal end (2*b*), and wherein said distal end is provided with a distal semi-tubular rounded extension (2*c*).

20 Claims, 4 Drawing Sheets

Figure 1:
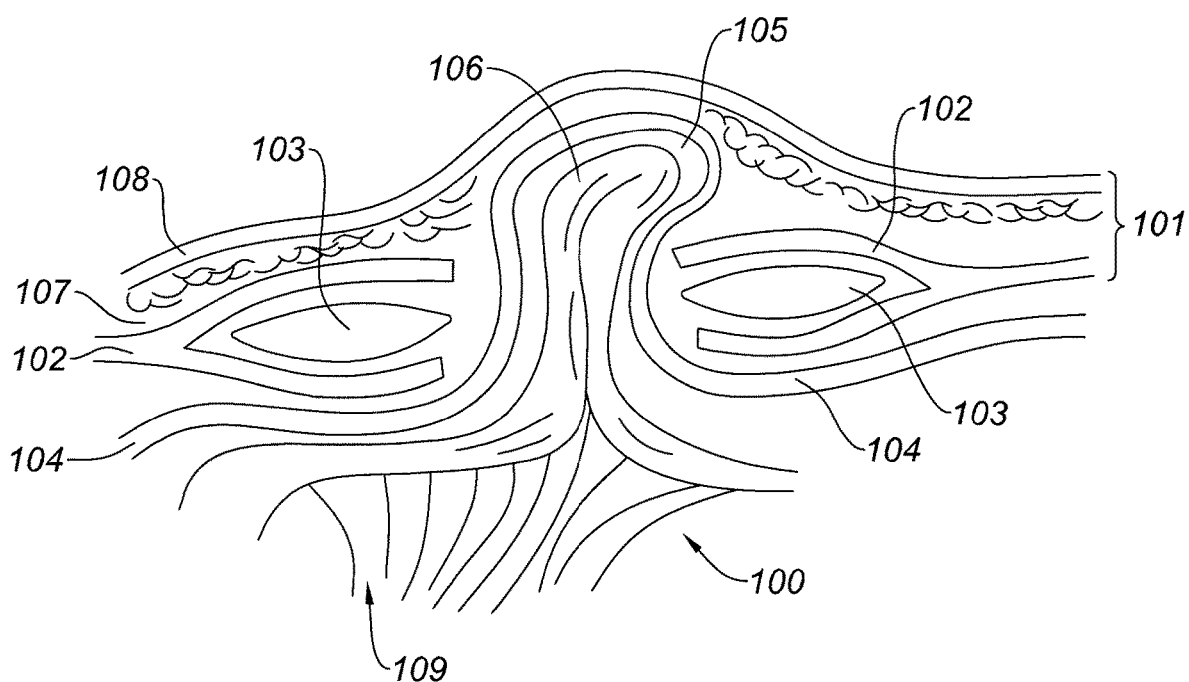

(52) U.S. Cl.
CPC .............. *A61F 2250/0091* (2013.01); *A61F 2250/0097* (2013.01)

(58) Field of Classification Search
CPC ...... A61F 2002/0068; A61F 2002/2484; A61F 2230/0008; A61F 2250/0091; A61F 2250/0097
See application file for complete search history.

(56) References Cited

U.S. PATENT DOCUMENTS

| | | | |
|---|---|---|---|
| 3,124,136 A | 3/1964 | Usher | |
| 3,272,204 A | 9/1966 | Artandi et al. | |
| 3,276,448 A | 10/1966 | Kronenthal | |
| 3,320,649 A | 5/1967 | Naimer | |
| 3,364,200 A | 1/1968 | Ashton et al. | |
| 3,570,482 A | 3/1971 | Shigeru et al. | |
| 4,006,747 A | 2/1977 | Kronenthal et al. | |
| 4,060,081 A | 11/1977 | Yannas et al. | |
| 4,173,131 A | 11/1979 | Melton et al. | |
| 4,193,137 A | 3/1980 | Heck | |
| 4,248,064 A | 2/1981 | Odham | |
| 4,294,241 A | 10/1981 | Miyata | |
| 4,307,717 A | 12/1981 | Hymes et al. | |
| 4,338,800 A | 7/1982 | Matsuda | |
| 4,476,697 A | 10/1984 | Schafer et al. | |
| 4,487,865 A | 12/1984 | Balazs et al. | |
| 4,500,676 A | 2/1985 | Balazs et al. | |
| 4,511,653 A | 4/1985 | Play et al. | |
| 4,527,404 A | 7/1985 | Nakagaki et al. | |
| 4,591,501 A | 5/1986 | Cioca | |
| 4,597,762 A | 7/1986 | Walter et al. | |
| 4,603,695 A | 8/1986 | Ikada et al. | |
| 4,631,932 A | 12/1986 | Sommers | |
| 4,670,014 A | 6/1987 | Huc et al. | |
| 4,709,562 A | 12/1987 | Matsuda | |
| 4,748,078 A | 5/1988 | Doi et al. | |
| 4,759,354 A | 7/1988 | Quarfoot | |
| 4,769,038 A | 9/1988 | Bendavid et al. | |
| 4,796,603 A | 1/1989 | Dahlke et al. | |
| 4,813,942 A | 3/1989 | Alvarez | |
| 4,841,962 A | 6/1989 | Berg et al. | |
| 4,854,316 A | 8/1989 | Davis | |
| 4,925,294 A | 5/1990 | Geshwind et al. | |
| 4,931,546 A | 6/1990 | Tardy et al. | |
| 4,942,875 A | 7/1990 | Hlavacek et al. | |
| 4,948,540 A | 8/1990 | Nigam | |
| 4,950,483 A | 8/1990 | Ksander et al. | |
| 4,970,298 A | 11/1990 | Silver et al. | |
| 5,002,551 A | 3/1991 | Linsky et al. | |
| 5,147,374 A | 9/1992 | Fernandez | |
| 5,162,430 A | 11/1992 | Rhee et al. | |
| 5,171,273 A | 12/1992 | Silver et al. | |
| 5,176,692 A | 1/1993 | Wilk et al. | |
| 5,192,301 A | 3/1993 | Kamiya et al. | |
| 5,196,185 A | 3/1993 | Silver et al. | |
| 5,201,745 A | 4/1993 | Tayot et al. | |
| 5,201,764 A | 4/1993 | Kelman et al. | |
| 5,206,028 A | 4/1993 | Li | |
| 5,217,493 A | 6/1993 | Raad et al. | |
| 5,254,133 A | 10/1993 | Seid | |
| 5,256,418 A | 10/1993 | Kemp et al. | |
| 5,263,983 A | 11/1993 | Yoshizato et al. | |
| 5,304,595 A | 4/1994 | Rhee et al. | |
| 5,306,500 A | 4/1994 | Rhee et al. | |
| 5,324,775 A | 6/1994 | Rhee et al. | |
| 5,328,955 A | 7/1994 | Rhee et al. | |
| 5,334,527 A | 8/1994 | Brysk | |
| 5,339,657 A | 8/1994 | Mcmurray | |
| 5,350,583 A | 9/1994 | Yoshizato et al. | |
| 5,356,432 A | 10/1994 | Rutkow et al. | |
| 5,368,549 A | 11/1994 | Mcvicker | |
| 5,376,375 A | 12/1994 | Rhee et al. | |
| 5,376,376 A | 12/1994 | Li | |
| 5,397,331 A | 3/1995 | Himpens et al. | |
| 5,399,361 A | 3/1995 | Song et al. | |
| 5,413,791 A | 5/1995 | Rhee et al. | |
| 5,425,740 A | 6/1995 | Hutchinson, Jr. | |
| 5,428,022 A | 6/1995 | Palefsky et al. | |
| 5,433,996 A | 7/1995 | Kranzler et al. | |
| 5,441,491 A | 8/1995 | Verschoor et al. | |
| 5,441,508 A | 8/1995 | Gazielly et al. | |
| 5,456,693 A | 10/1995 | Conston et al. | |
| 5,456,711 A | 10/1995 | Hudson | |
| 5,466,462 A | 11/1995 | Rosenthal et al. | |
| 5,480,644 A | 1/1996 | Freed | |
| 5,487,895 A | 1/1996 | Dapper et al. | |
| 5,490,984 A | 2/1996 | Freed | |
| 5,512,291 A | 4/1996 | Li | |
| 5,512,301 A | 4/1996 | Song et al. | |
| 5,514,181 A | 5/1996 | Light et al. | |
| 5,522,840 A | 6/1996 | Krajicek | |
| 5,523,348 A | 6/1996 | Rhee et al. | |
| 5,536,656 A | 7/1996 | Kemp et al. | |
| 5,543,441 A | 8/1996 | Rhee et al. | |
| 5,565,210 A | 10/1996 | Rosenthal et al. | |
| 5,567,806 A | 10/1996 | Abdul-Malak et al. | |
| 5,569,273 A | 10/1996 | Titone et al. | |
| RE35,399 E | 12/1996 | Eisenberg | |
| 5,593,441 A | 1/1997 | Lichtenstein et al. | |
| 5,595,621 A | 1/1997 | Light et al. | |
| 5,601,571 A | 2/1997 | Moss | |
| 5,607,474 A | 3/1997 | Athanasiou et al. | |
| 5,607,590 A | 3/1997 | Shimizu | |
| 5,614,587 A | 3/1997 | Rhee et al. | |
| 5,618,551 A | 4/1997 | Tardy et al. | |
| 5,634,931 A | 6/1997 | Kugel | |
| 5,639,796 A | 6/1997 | Lee | |
| 5,665,391 A | 9/1997 | Lea | |
| 5,667,839 A | 9/1997 | Berg | |
| 5,681,568 A | 10/1997 | Goldin et al. | |
| 5,686,115 A | 11/1997 | Vournakis et al. | |
| 5,690,675 A | 11/1997 | Sawyer et al. | |
| 5,695,525 A | 12/1997 | Mulhauser et al. | |
| 5,697,978 A | 12/1997 | Sgro | |
| 5,700,476 A | 12/1997 | Rosenthal et al. | |
| 5,700,477 A | 12/1997 | Rosenthal et al. | |
| 5,709,934 A | 1/1998 | Bell et al. | |
| 5,716,409 A | 2/1998 | Debbas | |
| 5,720,981 A | 2/1998 | Eisinger | |
| 5,732,572 A | 3/1998 | Litton | |
| 5,749,895 A | 5/1998 | Sawyer et al. | |
| 5,752,937 A | 5/1998 | Otten et al. | |
| 5,752,974 A | 5/1998 | Rhee et al. | |
| 5,766,246 A | 6/1998 | Mulhauser et al. | |
| 5,766,631 A | 6/1998 | Arnold | |
| 5,769,864 A | 6/1998 | Kugel | |
| 5,771,716 A | 6/1998 | Schlussel | |
| 5,785,983 A | 7/1998 | Furlan et al. | |
| 5,800,541 A | 9/1998 | Rhee et al. | |
| 5,814,328 A | 9/1998 | Gunasekaran | |
| 5,833,705 A | 11/1998 | Ken et al. | |
| 5,840,011 A | 11/1998 | Landgrebe et al. | |
| 5,861,034 A | 1/1999 | Taira et al. | |
| 5,863,984 A | 1/1999 | Doillon et al. | |
| 5,869,080 A | 2/1999 | Mcgregor et al. | |
| 5,871,767 A | 2/1999 | Dionne et al. | |
| 5,876,444 A | 3/1999 | Lai | |
| 5,891,558 A | 4/1999 | Bell et al. | |
| 5,899,909 A | 5/1999 | Claren et al. | |
| 5,906,937 A | 5/1999 | Sugiyama et al. | |
| 5,910,149 A | 6/1999 | Kuzmak | |
| 5,911,731 A | 6/1999 | Pham et al. | |
| 5,916,225 A | 6/1999 | Kugel | |
| 5,919,232 A | 7/1999 | Chaffringeon et al. | |
| 5,919,233 A | 7/1999 | Knopf et al. | |
| 5,922,026 A | 7/1999 | Chin | |
| 5,931,165 A | 8/1999 | Reich et al. | |
| 5,942,278 A | 8/1999 | Hagedorn et al. | |
| 5,962,136 A | 10/1999 | Dewez et al. | |
| 5,972,022 A | 10/1999 | Huxel | |
| RE36,370 E | 11/1999 | Li | |
| 5,993,844 A | 11/1999 | Abraham et al. | |
| 5,994,325 A | 11/1999 | Roufa et al. | |

(56) References Cited

U.S. PATENT DOCUMENTS

| | | |
|---|---|---|
| 5,997,895 A | 12/1999 | Narotam et al. |
| 6,001,895 A | 12/1999 | Harvey et al. |
| 6,008,292 A | 12/1999 | Lee et al. |
| 6,015,844 A | 1/2000 | Harvey et al. |
| 6,039,686 A | 3/2000 | Robert |
| 6,042,534 A | 3/2000 | Gellman et al. |
| 6,042,592 A | 3/2000 | Schmitt |
| 6,043,089 A | 3/2000 | Sugiyama et al. |
| 6,051,425 A | 4/2000 | Morota et al. |
| 6,056,688 A | 5/2000 | Benderev et al. |
| 6,056,970 A | 5/2000 | Greenawalt et al. |
| 6,057,148 A | 5/2000 | Sugiyama et al. |
| 6,063,396 A | 5/2000 | Kelleher |
| 6,066,776 A | 5/2000 | Goodwin et al. |
| 6,066,777 A | 5/2000 | Benchetrit |
| 6,071,292 A | 6/2000 | Makower et al. |
| 6,077,281 A | 6/2000 | Das |
| 6,080,194 A | 6/2000 | Pachence et al. |
| 6,083,522 A | 7/2000 | Chu et al. |
| 6,095,968 A | 8/2000 | Snyders |
| 6,120,539 A | 9/2000 | Eldridge et al. |
| 6,132,765 A | 10/2000 | Dicosmo et al. |
| 6,143,037 A | 11/2000 | Goldstein et al. |
| 6,153,292 A | 11/2000 | Bell et al. |
| 6,165,488 A | 12/2000 | Tardy et al. |
| 6,171,318 B1 | 1/2001 | Kugel et al. |
| 6,174,320 B1 | 1/2001 | Kugel et al. |
| 6,176,863 B1 | 1/2001 | Kugel et al. |
| 6,179,872 B1 | 1/2001 | Bell et al. |
| 6,197,325 B1 | 3/2001 | Macphee et al. |
| 6,197,934 B1 | 3/2001 | Devore et al. |
| 6,197,935 B1 | 3/2001 | Doillon et al. |
| 6,210,439 B1 | 4/2001 | Firmin et al. |
| 6,221,109 B1 | 4/2001 | Geistlich et al. |
| 6,224,616 B1 | 5/2001 | Kugel |
| 6,241,768 B1 | 6/2001 | Agarwal et al. |
| 6,258,124 B1 | 7/2001 | Darois et al. |
| 6,262,332 B1 | 7/2001 | Ketharanathan |
| 6,264,702 B1 | 7/2001 | Ory et al. |
| 6,267,772 B1 | 7/2001 | Mulhauser et al. |
| 6,277,397 B1 | 8/2001 | Shimizu |
| 6,280,453 B1 | 8/2001 | Kugel et al. |
| 6,287,316 B1 | 9/2001 | Agarwal et al. |
| 6,290,708 B1 | 9/2001 | Kugel et al. |
| 6,306,424 B1 | 10/2001 | Vyakarnam et al. |
| 6,312,474 B1 | 11/2001 | Francis et al. |
| 6,328,686 B1 | 12/2001 | Robert |
| 6,334,872 B1 | 1/2002 | Termin et al. |
| 6,383,201 B1 | 5/2002 | Dong |
| 6,391,333 B1 | 5/2002 | Li et al. |
| 6,391,939 B2 | 5/2002 | Tayot et al. |
| 6,408,656 B1 | 6/2002 | Ory et al. |
| 6,410,044 B1 | 6/2002 | Chudzik et al. |
| 6,413,742 B1 | 7/2002 | Olsen et al. |
| 6,428,978 B1 | 8/2002 | Olsen et al. |
| 6,436,030 B2 | 8/2002 | Rehil |
| 6,440,167 B2 | 8/2002 | Shimizu |
| 6,443,964 B1 | 9/2002 | Ory et al. |
| 6,447,551 B1 | 9/2002 | Goldmann |
| 6,447,802 B2 | 9/2002 | Sessions et al. |
| 6,448,378 B2 | 9/2002 | Devore et al. |
| 6,451,032 B1 | 9/2002 | Ory et al. |
| 6,451,301 B1 | 9/2002 | Sessions et al. |
| 6,454,787 B1 | 9/2002 | Maddalo et al. |
| 6,477,865 B1 | 11/2002 | Matsumoto |
| 6,479,072 B1 | 11/2002 | Morgan et al. |
| 6,500,464 B2 | 12/2002 | Ceres et al. |
| 6,509,031 B1 | 1/2003 | Miller et al. |
| 6,511,958 B1 | 1/2003 | Atkinson et al. |
| 6,514,286 B1 | 2/2003 | Leatherbury et al. |
| 6,514,514 B1 | 2/2003 | Atkinson et al. |
| 6,540,773 B2 | 4/2003 | Dong |
| 6,541,023 B1 | 4/2003 | Andre et al. |
| 6,548,077 B1 | 4/2003 | Gunasekaran |
| 6,554,855 B1 | 4/2003 | Dong |
| 6,559,119 B1 | 5/2003 | Burgess et al. |
| 6,566,345 B2 | 5/2003 | Miller et al. |
| 6,575,988 B2 | 6/2003 | Rousseau |
| 6,576,019 B1 | 6/2003 | Atala |
| 6,596,002 B2 | 7/2003 | Therin et al. |
| 6,596,304 B1 | 7/2003 | Bayon et al. |
| 6,599,323 B2 | 7/2003 | Melican et al. |
| 6,599,524 B2 | 7/2003 | Li et al. |
| 6,599,690 B1 | 7/2003 | Abraham et al. |
| 6,613,348 B1 | 9/2003 | Jain |
| 6,623,963 B1 | 9/2003 | Mueller et al. |
| 6,630,414 B1 | 10/2003 | Matsumoto |
| 6,638,284 B1 | 10/2003 | Rousseau et al. |
| 6,652,594 B2 | 11/2003 | Francis et al. |
| 6,653,450 B1 | 11/2003 | Berg et al. |
| 6,656,206 B2 | 12/2003 | Corcoran et al. |
| 6,660,280 B1 | 12/2003 | Allard et al. |
| 6,669,735 B1 | 12/2003 | Pelissier |
| 6,682,760 B2 | 1/2004 | Noff et al. |
| 6,685,714 B2 | 2/2004 | Rousseau |
| 6,706,684 B1 | 3/2004 | Bayon et al. |
| 6,706,690 B2 | 3/2004 | Reich et al. |
| 6,719,795 B1 | 4/2004 | Bryan et al. |
| 6,723,335 B1 | 4/2004 | Moehlenbruck et al. |
| 6,730,299 B1 | 5/2004 | Tayot et al. |
| 6,743,435 B2 | 6/2004 | Devore et al. |
| 6,755,868 B2 | 6/2004 | Rousseau |
| 6,773,723 B1 | 8/2004 | Spiro et al. |
| 6,790,213 B2 | 9/2004 | Cherok et al. |
| 6,790,454 B1 | 9/2004 | Abdul et al. |
| 6,800,082 B2 | 10/2004 | Rousseau |
| 6,833,408 B2 | 12/2004 | Sehl et al. |
| 6,835,336 B2 | 12/2004 | Watt |
| 6,852,330 B2 | 2/2005 | Bowman et al. |
| 6,869,938 B1 | 3/2005 | Schwartz et al. |
| 6,893,653 B2 | 5/2005 | Abraham et al. |
| 6,896,904 B2 | 5/2005 | Spiro et al. |
| 6,936,276 B2 | 8/2005 | Spiro et al. |
| 6,939,562 B2 | 9/2005 | Spiro et al. |
| 6,949,625 B2 | 9/2005 | Tayot |
| 6,966,918 B1 | 11/2005 | Schuldt-Hempe et al. |
| 6,971,252 B2 | 12/2005 | Therin et al. |
| 6,974,679 B2 | 12/2005 | Andre et al. |
| 6,974,862 B2 | 12/2005 | Ringeisen et al. |
| 6,977,231 B1 | 12/2005 | Matsuda |
| 6,988,386 B1 | 1/2006 | Okawa et al. |
| 7,025,063 B2 | 4/2006 | Snitkin et al. |
| 7,041,868 B2 | 5/2006 | Greene et al. |
| RE39,172 E | 7/2006 | Bayon et al. |
| 7,098,315 B2 | 8/2006 | Schaufler |
| 7,175,852 B2 | 2/2007 | Simmoteit et al. |
| 7,192,604 B2 | 3/2007 | Brown et al. |
| 7,207,962 B2 | 4/2007 | Anand et al. |
| 7,214,765 B2 | 5/2007 | Ringeisen et al. |
| 7,226,611 B2 | 6/2007 | Yura et al. |
| 7,229,453 B2 | 6/2007 | Anderson et al. |
| 7,594,921 B2 | 9/2009 | Browning |
| 7,670,380 B2 | 3/2010 | Cauthen, III et al. |
| 10,327,882 B2 * | 6/2019 | Bailly .................. A61F 2/0063 |
| 2001/0008930 A1 | 7/2001 | Tayot et al. |
| 2002/0095218 A1 | 7/2002 | Carr et al. |
| 2002/0116070 A1 | 8/2002 | Amara et al. |
| 2003/0013989 A1 | 1/2003 | Obermiller et al. |
| 2003/0023316 A1 | 1/2003 | Brown et al. |
| 2003/0086975 A1 | 5/2003 | Ringeisen |
| 2003/0100954 A1 | 5/2003 | Schuldt-Hempe et al. |
| 2003/0114937 A1 | 6/2003 | Leatherbury et al. |
| 2003/0133967 A1 | 7/2003 | Ruszczak et al. |
| 2003/0212460 A1 | 11/2003 | Darois et al. |
| 2003/0225355 A1 | 12/2003 | Butler |
| 2003/0232746 A1 | 12/2003 | Lamberti et al. |
| 2004/0034373 A1 | 2/2004 | Schuldt-Hempe et al. |
| 2004/0054406 A1 | 3/2004 | Dubson et al. |
| 2004/0059356 A1 | 3/2004 | Gingras |
| 2004/0101546 A1 | 5/2004 | Gorman et al. |
| 2004/0138649 A1 * | 7/2004 | Takamoto ............... A61B 17/11 606/1 |
| 2004/0138762 A1 | 7/2004 | Therin et al. |
| 2004/0172048 A1 | 9/2004 | Browning |

(56) References Cited

U.S. PATENT DOCUMENTS

| | | |
|---|---|---|
| 2004/0215219 A1 | 10/2004 | Eldridge et al. |
| 2005/0002893 A1 | 1/2005 | Goldmann |
| 2005/0010306 A1 | 1/2005 | Priewe et al. |
| 2005/0021058 A1 | 1/2005 | Negro |
| 2005/0085924 A1 | 4/2005 | Darois et al. |
| 2005/0113849 A1 | 5/2005 | Popadiuk et al. |
| 2005/0113938 A1 | 5/2005 | Jamiolkowski et al. |
| 2005/0137512 A1 | 6/2005 | Campbell et al. |
| 2005/0142161 A1 | 6/2005 | Freeman et al. |
| 2005/0148963 A1 | 7/2005 | Brennan |
| 2005/0175659 A1 | 8/2005 | Macomber et al. |
| 2005/0228408 A1 | 10/2005 | Fricke et al. |
| 2005/0232979 A1 | 10/2005 | Shoshan |
| 2005/0244455 A1 | 11/2005 | Greenawalt |
| 2005/0267521 A1 | 12/2005 | Forsberg |
| 2005/0288691 A1 | 12/2005 | Leiboff |
| 2006/0064175 A1 | 3/2006 | Pelissier et al. |
| 2006/0094318 A1 | 5/2006 | Matsuda et al. |
| 2006/0135921 A1 | 6/2006 | Wiercinski et al. |
| 2006/0147501 A1 | 7/2006 | Hillas et al. |
| 2006/0167561 A1 | 7/2006 | Odar et al. |
| 2006/0216320 A1 | 9/2006 | Kitazono et al. |
| 2006/0252981 A1 | 11/2006 | Matsuda et al. |
| 2007/0031474 A1 | 2/2007 | Tayot et al. |
| 2007/0112361 A1* | 5/2007 | Schonholz ............ A61F 2/0063 606/151 |
| 2007/0161109 A1 | 7/2007 | Archibald et al. |
| 2007/0213734 A1 | 9/2007 | Bleich et al. |
| 2007/0239254 A1 | 10/2007 | Chia et al. |
| 2007/0280990 A1 | 12/2007 | Stopek |
| 2007/0297987 A1 | 12/2007 | Stad et al. |
| 2007/0299538 A1 | 12/2007 | Roeber |
| 2008/0306497 A1 | 12/2008 | Brown et al. |
| 2011/0022165 A1* | 1/2011 | Oba ................... A61B 17/3468 623/2.11 |
| 2011/0034942 A1* | 2/2011 | Levin ............... A61B 17/00234 606/151 |
| 2011/0301502 A1 | 12/2011 | Gill |
| 2013/0331868 A1 | 12/2013 | Lepage, Jr. et al. |
| 2014/0249540 A1 | 9/2014 | Nieman et al. |
| 2014/0379007 A1 | 12/2014 | Costa et al. |

FOREIGN PATENT DOCUMENTS

| | | |
|---|---|---|
| DE | 10019604 A1 | 10/2001 |
| DE | 10043396 C1 | 6/2002 |
| EP | 0194192 A1 | 9/1986 |
| EP | 0248544 A1 | 12/1987 |
| EP | 0276890 A2 | 8/1988 |
| EP | 0372969 A1 | 6/1990 |
| EP | 0544485 A1 | 6/1993 |
| EP | 0552576 A1 | 7/1993 |
| EP | 0614650 A2 | 9/1994 |
| EP | 0621014 A1 | 10/1994 |
| EP | 0625891 A1 | 11/1994 |
| EP | 0637452 A1 | 2/1995 |
| EP | 0705878 A2 | 4/1996 |
| EP | 0719527 A1 | 7/1996 |
| EP | 0774240 A1 | 5/1997 |
| EP | 0797962 A2 | 10/1997 |
| EP | 0827724 A2 | 3/1998 |
| EP | 0836838 A1 | 4/1998 |
| EP | 0895762 A2 | 2/1999 |
| EP | 0898944 A2 | 3/1999 |
| EP | 1017415 A1 | 7/2000 |
| EP | 1052319 A1 | 11/2000 |
| EP | 1055757 A1 | 11/2000 |
| EP | 1216717 A1 | 6/2002 |
| EP | 1216718 A1 | 6/2002 |
| EP | 0693523 B1 | 11/2002 |
| EP | 1315468 A2 | 6/2003 |
| EP | 1382728 A1 | 1/2004 |
| EP | 1484070 A1 | 12/2004 |
| EP | 1561480 A2 | 8/2005 |
| EP | 1782848 A2 | 5/2007 |
| EP | 2633827 A1 | 9/2013 |
| EP | 2712580 A1 | 4/2014 |
| FR | 2244853 A1 | 4/1975 |
| FR | 2257262 A1 | 8/1975 |
| FR | 2308349 A1 | 11/1976 |
| FR | 2453231 A1 | 10/1980 |
| FR | 2715405 A1 | 7/1995 |
| FR | 2724563 A1 | 3/1996 |
| FR | 2744906 A1 | 8/1997 |
| FR | 2766698 A1 | 2/1999 |
| FR | 2771622 A1 | 6/1999 |
| FR | 2779937 A1 | 12/1999 |
| FR | 2859624 A1 | 3/2005 |
| FR | 2863277 A1 | 6/2005 |
| FR | 2884706 A1 | 10/2006 |
| GB | 2051153 A | 1/1981 |
| JP | H0332677 A | 2/1991 |
| JP | H05237128 A | 9/1993 |
| JP | H09137380 A | 5/1997 |
| WO | 8902445 A1 | 3/1989 |
| WO | 8908467 A1 | 9/1989 |
| WO | 9012551 A1 | 11/1990 |
| WO | 9206639 A2 | 4/1992 |
| WO | 9220349 A1 | 11/1992 |
| WO | 9311805 A1 | 6/1993 |
| WO | 9318174 A1 | 9/1993 |
| WO | 9417747 A1 | 8/1994 |
| WO | 9507666 A1 | 3/1995 |
| WO | 9518638 A1 | 7/1995 |
| WO | 9532687 A1 | 12/1995 |
| WO | 9603091 A1 | 2/1996 |
| WO | 9608277 A1 | 3/1996 |
| WO | 9609795 A1 | 4/1996 |
| WO | 9614805 A1 | 5/1996 |
| WO | 9641588 A1 | 12/1996 |
| WO | 9735533 A1 | 10/1997 |
| WO | 9835632 A1 | 8/1998 |
| WO | 9849967 A1 | 11/1998 |
| WO | 9905990 A1 | 2/1999 |
| WO | 9906079 A1 | 2/1999 |
| WO | 9906080 A1 | 2/1999 |
| WO | 9951163 A1 | 10/1999 |
| WO | 0016821 A1 | 3/2000 |
| WO | 0067663 A1 | 11/2000 |
| WO | 0115625 A1 | 3/2001 |
| WO | 0180773 A1 | 11/2001 |
| WO | 0207648 A1 | 1/2002 |
| WO | 02078568 A1 | 10/2002 |
| WO | 03002168 A1 | 1/2003 |
| WO | 2004004600 A1 | 1/2004 |
| WO | 2004071349 A2 | 8/2004 |
| WO | 2004078120 A2 | 9/2004 |
| WO | 2004103212 A1 | 12/2004 |
| WO | 2005011280 A1 | 2/2005 |
| WO | 2005013863 A2 | 2/2005 |
| WO | 2005018698 A1 | 3/2005 |
| WO | 2005105172 A1 | 11/2005 |
| WO | 2006018552 A1 | 2/2006 |
| WO | 2006023444 A2 | 3/2006 |
| WO | 2007048099 A2 | 4/2007 |
| WO | 2007056297 A2 | 5/2007 |
| WO | 2013007534 A1 | 1/2013 |
| WO | 2013048272 A1 | 4/2013 |

OTHER PUBLICATIONS

Blondin, C. et al., "Inhibition of Complement Activation by Natural Sulfated Polysaccharides (Fucans) from Brown Seaweed," Molecular Immuol., Mar. 1994, pp. 247-253, 31(4).

Blondin, C. et al., "Relationships between chemical characteristics and anticomplementary activity of fucans," Biomaterials, Mar. 1996, pp. 597-603, 17(6).

Boisson-Vidal, C. et al., "Neoangiogenesis Induced by Progenitor Endothelial Cells: Effect of Fucoidan From Marine Algae," Cardiovascular & Hematological Agents in Medicinal Chem., Jan. 2007, pp. 67-77, 5(1).

(56) References Cited

OTHER PUBLICATIONS

Bracco, P. et al., "Comparison of polypropylene and polyethylene terephthalate (Dacron) meshes for abdominal wall hernia repair: A chemical and morphological study," Hernia, 2005, pp. 51-55, 9 (1), published online Sep. 2004.
Collins, R. et al., "Use of collagen film as a dural substitute: Preliminary animal studies," Journal of Biomedical Materials Research, Feb. 1991, pp. 267-276, vol. 25.
Ellouali, M. et al., "Antitumor Activity of Low Molecular Weight Fucans Extracted from Brown Seaweed Ascophyllum nodosum," Anticancer Res., Nov.-Dec. 1993, pp. 2011-2020, 12 (6A).
European Search Report for EP 14306522.5 date of completion is Apr. 17, 2015 (7 pages).
Examination report No. 1 issued in corresponding Australian patent application No. 2015221458 dated May 14, 2019, 6 pages.
Haneji, K. et al., "Fucoidan extracted from Cladosiphon Okamuranus Tokida Induces Apoptosis of Human T-cell Leukemia Virus Type 1-Infected T-Cell Lines and Primary Adult T-Cell Leukemia Cells," Nutrition and Cancer, 2005, pp. 189-201, 52(2), published online Nov. 2009.
Haroun-Bouhedja, F. et al., "In Vitro Effects of Fucans on MDA-MB231 Tumor Cell Adhesion and Invasion," Anticancer Res., Jul.-Aug. 2002, pp. 2285-2292, 22(4).
Haroun-Bouhedja, F. et al., "Relationship between sulfate groups and biological activities of fucans," Thrombosis Res., Dec. 2000, pp. 453-459, 100(5).
Hirano, S. et al., "The blood biocompatibility of chitosan and N-acylchitosans," J. Biomed. Mater. Res., Apr. 1985, 413-417, 19.
Junge, K. et al., "Functional and Morphologic Properties of a Modified Mesh for Inguinal Hernia Repair," World J. Surg., Sep. 2002, pp. 1472-1480, 26.
Kanabar, V. et al., "Some structural determinants of the antiproliferative effect of heparin-like molecules on human airway smooth muscle," Br. J. Pharmacol., Oct. 2005, pp. 370-777, 146(3).
Klinge, U. et al., "Foreign Body Reaction to Meshes Used for the Repair of Abdominal Wall Hernias," Eur J. Surg, Sep. 1999, pp. 665-673, 165.
Klinge, U. et al., "Functional and Morphological Evaluation of a Low-Weight, Monofilament Polypropylene Mesh for Hernia Repair," J Biomed. Mater. Res., Jan. 2002, pp. 129-136, 63.
Langenbech, M. R. et al., "Comparison of biomaterials in the early postoperative period," Surg Enclose., May 2003, pp. 1105-1109, 17(7).
Logeart, D. et al., "Fucans, sulfated polysaccharides extracted from brown seaweeds, inhibit vascular smooth muscle cell proliferation. II. Degradation and molecular weight effect," Eur. J. Cell. Biol., Dec. 1997, pp. 385-390, 74(4).
Malette, W. G. et al., "Chitosan, a New Hemostatic," Ann Th. Surg., Jul. 1983, pp. 55-58, 36.
Muzzarelli, R. et al., "Reconstruction of parodontal tissue with chitosan," Biomaterials, Nov. 1989, pp. 598-604, 10.
O'Dwyer, P. et al., "Randomized clinical trial assessing impact of a lightweight or heavyweight mesh on chronic pain after inguinal hernia repair," Br. J. Surg., Feb. 2005, pp. 166-170, 92(2).
Preliminary Search Report from French Patent Office dated Dec. 20, 2006, 3 pages.
Prokop, A. et al., "Water Soluble Polymers for Immunoisolation I: Complex Coacevation and Cytotoxicity," Advances in Polymer Science, Jul. 1998, pp. 1-51, 136.
Rao, B. et al., "Use of chitosan as a biomaterial: Studies on its safety and hemostatic potential," J. Biomed. Mater. Res., Jan. 1997, pp. 21-28, 34.
Rosen, M. et al., "Laparoscopic component separation in the single-stage treatment of infected abdominal wall prosthetic removal," Hernia, 2007, pp. 435-440,11, published online Jul. 2007.
Scheidbach, H. et al., "In vivo studies comparing the biocompatibility of various polypropylene meshes and their handling properties during endoscopic total extraperitoneal (TEP) patchplasty: An experimental study in pigs," Surg. Endosc., Feb. 2004, pp. 211-220, 18(2).
Strand, S. et al., "Screening of Chitosans and Conditions for Bacterial Flocculation," Biomacromolecules, Mar. 2001, 126-133, 2.
Varum, K. et al., "In vitro degradation rates of partially N-acetylated chitosans in human serum," Carbohydrate Research, Mar. 1997, pp. 99-101, 299.
Welty, G. et al., "Functional impairment and complaints following incisional hernia repair with different polypropylene meshes," Hernia, Aug. 2001; pp. 142-147, 5.
Zvyagintseva, T. et al., "Inhibition of complement activation by water-soluble polysaccharides of some far-eastern brown seaweeds," Comparative Biochem and Physiol, Jul. 2000, pp. 209-215, 126(3).
Communication pursuant to Article 94(3) EPC issued in European Patent Application No. 14306522.5 dated Oct. 24, 2019, 5 pages.
Canadian Office Action issued in Canadian Application No. 2,902,563 dated Sep. 16, 2021, 5 pages.

* cited by examiner

WHALE CONCEPT-FOLDING MESH FOR TIPP PROCEDURE FOR INGUINAL HERNIA

CROSS-REFERENCE TO RELATED APPLICATIONS

This application is a continuation of U.S. patent application Ser. No. 14/860,748 filed Sep. 22, 2015, which claims benefit of and priority to European Patent Application Serial No. 14306522.5 filed Sep. 29, 2014, and the disclosures of each of the above-identified applications are hereby incorporated by reference in their entirety.

The present invention provides a device for introducing a flexible prosthesis, for example for repairing hernias, in an incision of small size. The present invention further relates to a kit comprising such a device and a flexible prosthesis intended to be introduced in a patient via said device.

In this application, the "medial" end or part of an element of a prosthesis is to be understood as meaning the end or part of the element located in the direction of the median plane of the body when the prosthesis is implanted in the body. The "lateral" end or part of an element of a prosthesis is to be understood as meaning the end or part of the element located in the direction of the outwards lateral plane of the body when the prosthesis is implanted in the body. Likewise, in this application, the "medial direction" is to be understood as meaning the direction towards said median plane and the "lateral direction" is opposite the "medial direction", the medial and lateral directions being aligned on the same axis, the medial-lateral axis. In this application, the "cranial" end or part of an element of a prosthesis is to be understood as meaning the end or part of the element located substantially in the direction of the head of the body when the prosthesis is implanted in the body. The "caudal" end or part of an element of a prosthesis is to be understood as meaning the end or part of the element located in the direction of the feet of the body when the prosthesis is implanted in the body. Likewise, in this application, the "cranial direction" is to be understood as meaning the direction towards said head and the "caudal direction" is opposite the "cranial direction", the cranial and caudal directions being aligned on the same axis, the cranial-caudal axis.

In humans the abdominal wall consists of fat and muscles interconnected by aponeuroses. A break in continuity may occur at the level of the aponeuroses, allowing part of the peritoneum to pass through and form a sac, known as a hernia, containing either fat or a portion of the intestine. Hernias or ventral ruptures (hernias occurring on a parietal surgical scar) are manifested by a protrusion on the surface of the skin and are called umbilical or inguinal hernias or ventral ruptures, for example, as a function of their location.

To repair a hernia, surgeons often fit a synthetic mesh prosthesis that replaces or reinforces the weakened anatomical tissue.

In the case of umbilical or inguinal hernias, for example, or when the aim of treatment is to repair trocar holes or preventive, the size of the defect to be treated is small, for example from 1 to 4 cm diameter, and open surgery may be envisaged without widening the defect. However, in this type of surgery, the surgeon has little working space and little visibility. It would be desirable to have in possession a device suitable for introducing the prosthesis into such a small incision without having to grasp the prosthesis with an additional instrument. It would also be desirable that the prosthesis does not touch the incision edges during the introduction step.

Some flexible prostheses, such as textile based prostheses, may be adapted to occupy a small volume in a first configuration in which they are folded up on themselves and to be deployed and spread out in a second configuration corresponding to an implantation configuration.

Various prostheses that may be folded up and then deployed are available. Some of them are provided with a resilient reinforcing element capable of automatically restoring its initial shape to the prosthesis after said prosthesis has been folded up on itself.

Inguinal hernias relate to defects to be treated in the inguinal anatomical region. The inguinal region comprises the intersection of a parietal plane comprising the orifice of the inguinal canal and of a vascular plane comprising the iliac vessels and the spermatic cord when the patient is a man. The shape of a prosthesis intended to be used for treating an inguinal hernia will be asymmetric and dependent on the side (right or left) of the body that is to be treated. In this view, the shape of a prosthesis for treating an inguinal hernia may be defined in relation with the position of the prosthesis once implanted in the body of a patient. For example, in an implanted configuration, a prosthesis for treating an inguinal hernia comprises a medial part, a lateral part, a caudal part, and a cranial part as defined above. A prosthesis intended to be used in the treatment of an inguinal hernia will generally have an elongate shape with a longitudinal axis substantially aligned on the medial-lateral axis of the body.

A first aspect of the present invention is a device for introducing a flexible textile based prosthesis into a surgical incision, comprising a globally tubular body having a proximal end and a distal end, said tubular body being designed for receiving the prosthesis in a folded configuration in a sliding way, wherein the tubular body has a substantially oblong cross-section and is provided with an open longitudinal slit extending from said proximal end to said distal end.

In this application, the distal end of a component or of a device is to be understood as meaning the end furthest from the surgeon's body and the proximal end is to be understood as meaning the end closest to the surgeon's body when the surgeon is completing the surgical operation. Likewise, in this application, the "distal direction" is to be understood as meaning the direction of implantation, namely towards the patient body, and the "proximal direction" is to be understood as meaning the opposite direction to said direction of implantation.

Thanks to the shape of the device and of the presence of the longitudinal slit, the prosthesis may be easily folded up and introduced into the device without having to use an additional tool. The oblong cross section of the tubular body is particularly adapted for a facilitated progression of a folded prosthesis inside the device. Furthermore, the walls of the tubular body of the device allow the prosthesis to avoid touching the incision edges in an open surgery method, even if the incision is of very small size, for example is less than 4 cm or 3 cm long.

The presence of the longitudinal slit in the device of the invention also allows compression of the walls of the tubular body and therefore reduction of the cross sectional area of the device, thereby facilitating the insertion of the device into the incision. The presence of the longitudinal slit further allows a direct access to the prosthesis by a hand of the surgeon for example or by a tool, for maintaining the prosthesis into the body of the patient at the time the device of the invention is removed from the incision.

As will appear from the description below, the device of the invention allows a standardized gesture of the surgeon. The device of the invention guarantees the surgeon that the incision he has made is sufficient and that the prosthesis will be delivered at the right place. The device of the invention further allows the surgeon to confirm and or redesign the dissection he has made at the implantation site.

In embodiments, said distal end is provided with a distal semi-tubular rounded extension. The distal semi-tubular rounded extension may for example have the global shape of a spatula. The distal semi-tubular rounded extension of the distal end of the device allows an easy introduction of the device into a small incision, for example an incision of 3 or 4 cm long. The rounded shape of the distal semi-tubular extension will not damage the surrounding biological tissues, such as the peritoneum. In addition, the distal semi-tubular rounded extension may be used for further dissection if the dissection pocket completed by the surgeon in the first place proves to be too small in the end.

In embodiments, the proximal end is provided with a proximal semi-tubular extension forming a partial funnel. Such a shape allows an easier introduction of the folded prosthesis in the tubular body. In addition, such a shape helps an automatic folding of the prosthesis into the tubular body, as the sloped walls of the proximal end of the tubular body naturally urge the prosthesis towards the inside of the tubular body.

In embodiments, said device comprises markings defining a ruler. For example, markings are provided on the tubular body for forming a ruler. Such markings may help the surgeon determine whether he has dissected an adequately long enough pocket for the insertion of the prosthesis. Such markings are more accurate than the "finger" measurement system usually used by surgeons. Such markings may therefore help avoid the situation where the surgeon attempts to position the prosthesis at the implantation site only to discover that he has not dissected enough and that he must remove the prosthesis, dissect further and then re-introduce the prosthesis. Such embodiments with markings therefore allow saving time and avoiding potential irritation and infection.

In embodiments, the tubular body is made of a transparent material. Such embodiments allow a good visibility of the folded prosthesis inside the tubular body. Such embodiments allow the surgeon to check the sliding and movement of the prosthesis from the proximal end of the tubular body to its distal end up to the ejection of the prosthesis from the device of the invention.

In embodiments, the tubular body is made from a material selected from poly(ethylene terephthalate) glycol (PETG), polyethylene terephthalate (PET), polypropylene, polycarbonate and mixtures thereof. These materials provide to the walls of the tubular body a smooth surface facilitating on one hand the sliding of the prosthesis inside the tubular body and easing on the other hand the introduction of the device in the incision.

Another aspect of the present invention is a kit comprising a device as described above and a prosthesis of generally elongate shape defining a longitudinal axis A aligned on a medial-lateral axis and a transversal axis B aligned on a cranial-caudal axis, said prosthesis comprising:

at least one flexible biocompatible textile of elongate shape comprising a medial end, a lateral end, a cranial part and a caudal part, said textile being delimited by a peripheral outer edge formed of a convex medial edge, a convex cranial edge, a convex lateral edge and a caudal edge, and at least one reinforcing element for said textile, said reinforcing element being in the form of a resilient frame connected to said textile and set back from the peripheral outer edge.

According to the present invention, "textile" is understood as any arrangement or assembly of biocompatible yarns, fibres, filaments and/or multifilaments, for example obtained by knitting, weaving, braiding, or non-woven.

In the present application, "biocompatible" is understood as meaning that the materials having this property can be implanted in the human or animal body.

Within the meaning of the present application, a "flexible textile" is understood as a textile that can be folded up but that does not have an inherent elasticity allowing it to spontaneously recover a spread-out configuration once it has been folded up.

Within the meaning of the present application, a "resilient frame" is understood as a frame which, for example, can be semi-rigid and has a resiliency or elasticity allowing it to be deformed under the effect of a temporary stress and allowing it to return to an initial state of rest once said stress has been removed. According to the present invention, the frame allows the textile, and therefore the prosthesis, to be pressed together in the transversal direction towards the longitudinal axis of the textile.

The prosthesis above is intended to be introduced in the body of the patient and to be conveyed to the implantation site with the device of the invention. The prosthesis is able to be folded up along at least one folding direction in a very simple way, for example by pressing the frame together, in one hand, transversally in the direction of the longitudinal axis of the prosthesis. Thus, the prosthesis is capable of adopting an elongate configuration, which is very compact in the transversal direction, allowing it to be introduced in the tubular body of the device of the invention. The frame is sufficiently resilient to allow the prosthesis to be folded in order to enter the proximal end of the tubular body. When the prosthesis emerges from the distal end of the tubular body, it tends to spread out automatically under the action of the frame, which tends to recover its initial configuration in the absence of the stresses from the walls of the tubular body. The prosthesis is capable of conforming to the anatomical structures and of remaining in place once it is positioned at the implantation site.

In embodiments, the frame comprises a convex cranial segment extending from the medial end of the textile to the lateral end of said textile along said convex cranial edge, a caudal segment substantially extending from the medial end of the textile to the lateral end of said textile and caudally spaced with respect to said convex cranial segment, a lateral corner segment joining together the convex cranial segment and the caudal segment in the region of the lateral end of the textile, and a folding segment configured for joining a medial end of said convex cranial segment to a point located on the caudal segment while leaving the region of the medial end of the textile free of any frame, said frame being able to adopt an unstressed configuration, in which said textile is deployed, and a stressed configuration, in which said frame is subjected to a transversal force directed towards said longitudinal axis A, and said convex cranial segment, said caudal segment and said folding segment are substantially collected together and aligned on one folding direction, said textile forming thereby at least one fold along said folding direction.

The specific shape of the frame allows facilitating the folding of the prosthesis and thus its introduction in the device of the invention. The respective shapes of the convex cranial segment, the caudal segment and the folding segment allow these segments to be able to converge together and to be aligned on one folding direction when a transversal pressure is exerted on the frame. The absence of any frame structure in the region of the medial end of the textile allows the convex cranial segment and the caudal segment to be brought close together, for example side by side or alternatively one on the top of the other, at the time of the folding of the prosthesis. The transversal volume occupied by the prosthesis is therefore reduced, making it easier to introduce the prosthesis into the proximal end of the tubular body of the device of the invention, in the direction of the longitudinal axis of the prosthesis.

The materials that may be suitable for producing the frame of the prosthesis according to the kit of the invention may be chosen from any biocompatible material having a certain rigidity in order to meet the requirements described above.

In one embodiment, the frame is made of a bioresorbable material. In the present application, "bioresorbable" or "biodegradable" is understood to mean that the materials having this property are absorbed and/or degraded by the tissues or washed from the implantation site and disappear in vivo after a certain time, which may vary, for example, from a few hours to a few months, depending on the chemical nature of the materials.

Thus, the frame may act as a guide for the prosthesis for introducing said prosthesis into the tubular body of the device of the invention, then may act as a means of stiffening the prosthesis during the positioning and implanting of the prosthesis, after which it may gradually degrade when the textile has been recolonized by the surrounding cells.

For example, the bioresorbable material can be chosen from among polylactic acid (PLA), polycaprolactones (PCL), polydioxanones (PDO), trimethylene carbonates (TMC), polyvinyl alcohol (PVA), polyhydroxyalkanoates (PHA), oxidized cellulose, polyglycolic acid (PGA), copolymers of these materials and mixtures thereof. For example, the bioresorbable material can be a copolymer of polylactic acid and of polyglycolic acid.

Alternatively, the frame of the prosthesis according to the invention is made of a non-bioresorbable material chosen from among polypropylenes, polyesters such as polyethyleneterephthalates, polyamides, silicones, polyether ether ketone (PEEK), polyarylether ether ketone (PAEK), polyurethanes and mixtures thereof.

In another embodiment, said frame is formed by a combination of bioresorbable material and of non-bioresorbable material.

In the prosthesis of the kit of the invention, the caudal segment of the frame may serve as a positioning guide for the surgeon, this caudal segment preferably having to be placed in the inguinal region at the intersection of the parietal and vascular planes to permit optimal positioning of the prosthesis. In one embodiment of the invention, said caudal segment may form a fold of the textile, said fold causing said caudal part of said textile to form naturally an angle to the plane of said cranial part of said textile. Thus, the caudal segment may give the textile a three-dimensional shape, similar to the anatomy of the inguinal region, by forming a fold in the textile, in such a way that the caudal part of the textile tends naturally to form an angle with the cranial part of said textile, this angle corresponding to the angle formed anatomically by the intersection of the parietal and vascular planes.

In embodiments, said caudal segment is concave. Such a shape allows an easy pressing of the frame and therefore of the prosthesis, and a significant reduction of the volume occupied by the prosthesis in the transversal direction. In addition, the concavity of the caudal segment confers to the caudal part of the textile an undulated and anatomical developed shape for matching the general shape of the lower inguinal structures, especially the spermatic and iliac vessels and the psoas muscle.

In embodiments, the folding segment joins the medial end of said convex cranial segment to a medial end of the caudal segment. For example, the folding segment has a U shape extending towards a center of the textile. In such embodiments, when pressing the frame transversally, the two legs of the U of the folding segment converge together with the convex cranial segment and the caudal segment, allowing a significant reduction of the volume occupied by the prosthesis in the transversal direction.

In one embodiment, said frame is continuous. Thus, the step of pressing the prosthesis together, by pressing the frame together towards the longitudinal axis of the prosthesis, does not create any projecting elements that could potentially perforate and damage the tissues. By virtue of its nature and its shape, the frame only has rounded and atraumatic outer contours.

In embodiments, at least a part of said frame, for example at least a part of the caudal segment, has substantially the structure of a flat band forming undulations substantially in the plane of said textile. Such undulations allow a good conformability of the prosthesis in general, and a good flexibility to the caudal segment in particular at the intersection of the parietal and vascular planes. Such undulations can expand and contract to further confer a greater flexibility to the frame. The step of introducing the prosthesis inside the tubular body of the device of the invention is therefore facilitated. In addition, such undulations confer a good resistance to folding to the prosthesis.

In embodiments, said frame further comprises a caudal extension located on the caudal segment and extending in the caudal direction toward the caudal edge of the textile. The caudal extension helps deploying the caudal part of the textile once the prosthesis is implanted. This caudal extension helps spreading out the caudal part of the textile on the biological tissues it is intended to cover, namely the iliac and spermatic vessels and part of the psoas muscle.

The frame of the prosthesis according to the invention is connected to said textile. For example, the frame can be fixed to the textile by sewing, ultrasonic welding, or else by adhesive bonding or moulding.

In one embodiment, the frame of the prosthesis according to the kit of the invention is moulded over the textile. Thus, the frame is connected to the textile by injection moulding of one or more thermoplastic or thermosetting biocompatible materials. For example, the mould of an injection-moulding machine is equipped with an insert gate in which the textile is held. One or more thermoplastic or thermosetting biocompatible materials are then heated to their melting point and injected into the mould, the latter having one or more channels of the shape desired for the frame. The holding of the textile, the precision of the injection volume and the choice of the injection parameters make it possible to obtain a frame without material loss, without flash and with good surface evenness. Such a method allows the frame to be fixed to the textile in a particularly effective and lasting way.

In one embodiment, the frame is obtained by moulding a copolymer of polylactic acid and of polyglycolic acid over the textile.

The textile of the prosthesis according to the kit of the invention has a generally elongate shape, for example oval or elliptic. The textile can have another initial shape and can then be cut to such an elongate shape, in particular to a shape adapted to the defect, for example the hernia defect of the inguinal region, that is to be treated. In particular, the shape of the textile of the prosthesis of the invention comprises a part capable of efficiently covering the anterior muscle wall, the orifice of the inguinal canal, the upper part of the os pubis and Cooper's ligament, and a part capable of covering efficiently the iliac vessels and spermatic vessels and part of the psoas muscle. The textile is delimited by a peripheral outer edge formed of a convex medial edge, a convex cranial edge, a convex lateral edge and a caudal edge. The caudal edge may be flat or convex. Preferably, the caudal edge is convex in order to optimize the covering of the iliac vessels and spermatic vessels and part of the psoas muscle. As such, the general shape of the peripheral outer edge is preferably convex.

The textile may be bioresorbable, permanent or partially bioresorbable. In embodiments, the textile is bioresorbable. Bioresorbable textiles may be made from low density meshes or knit designs. In embodiments, for example when the prosthesis is not intended to remain permanently in the body of a patient, both the frame and the textile are bioresorbable. For example, the frame is bioresorbable in a time frame comparable to the textile. The shape and nature of the frame of the prosthesis of the invention allow providing a prosthesis based on a low density bioresorbable textile capable of offering sufficient strength for performing its repair function and sufficient rigidity for being efficiently manipulated while at the same time limiting the amount of foreign material implanted.

In one embodiment, the textile is a mesh.

Within the meaning of the present application, a "mesh" is understood as a textile, as defined above, which is openworked, that is to say provided with pores that favour recolonization of tissue. It is sufficiently flexible to be folded up at the time of introduction into the abdominal cavity. The mesh can be made from a layer of textile or several layers of textile. Such meshes are well known to a person skilled in the art.

In one embodiment of the invention, the mesh is a knit. By virtue of the meshwork of the knit, it is possible to obtain openworked faces that promote cell recolonization after implantation.

Another aspect of the present invention is a method by which a prosthesis as described above is conveyed to an implantation site of the inguinal region during an open surgery procedure, said method comprising the following steps:
- an incision of size ranging from 3 to 4 cm is completed on the abdominal skin,
- the above prosthesis is pressed together and/or folded upon itself, by applying a transversal pressure on the frame, so that said textile forms a fold along the folding direction, and said convex cranial segment, said caudal segment and said folding segment are substantially collected together, for example side by side or one on top of the other, and aligned on one folding direction,
- the medial end of the prosthesis is approached towards the proximal end of the tubular body of the device of the invention and the folded prosthesis is at least partially introduced into the tubular body,
- the distal end of the tubular body is introduced into the incision and pushed in the distal direction up to the implantation site,
- the surgeon pushes distally on the prosthesis so as to make it slide into the tubular body and be conveyed to the implantation site in the inguinal region,
- the surgeon maintains the prosthesis in place by accessing the prosthesis via the longitudinal slit while pulling on the tubular body in the proximal direction for removing the device of the invention from the body of the patient,
- when the device of the invention is removed, the pressure previously exerted on the frame by the walls of the tubular body is released and the prosthesis automatically starts deploying by means of the frame tending to come back to its unstressed configuration.

Figure 2:
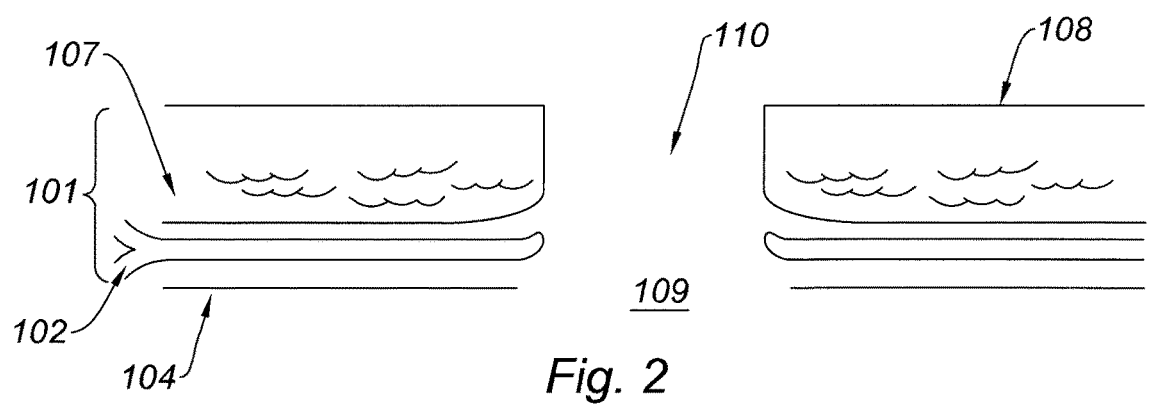
Figure 3:
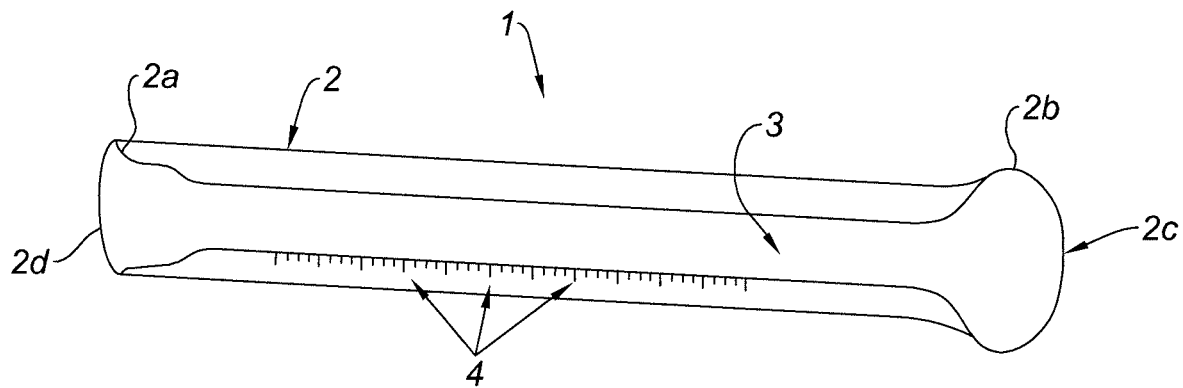
Figure 4:
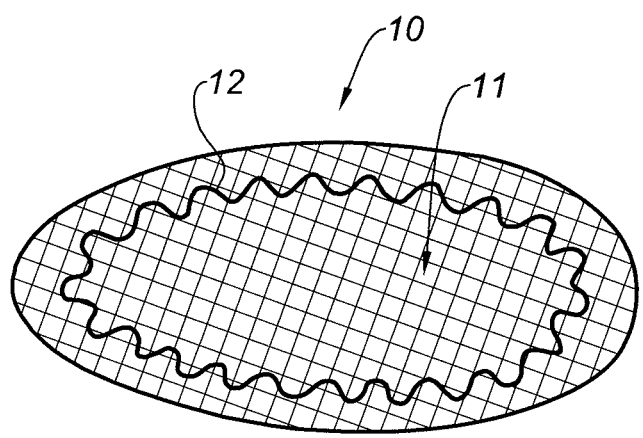
Figure 5:
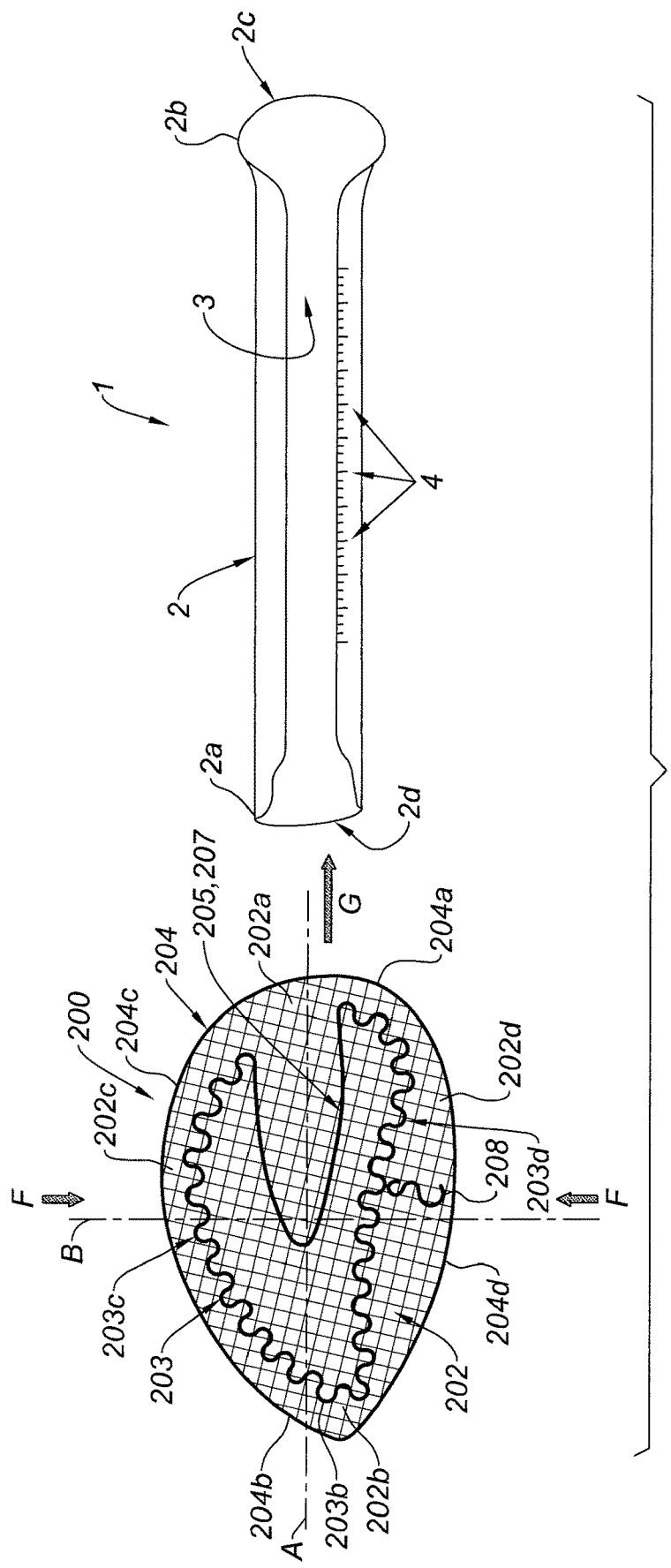
Figure 6:
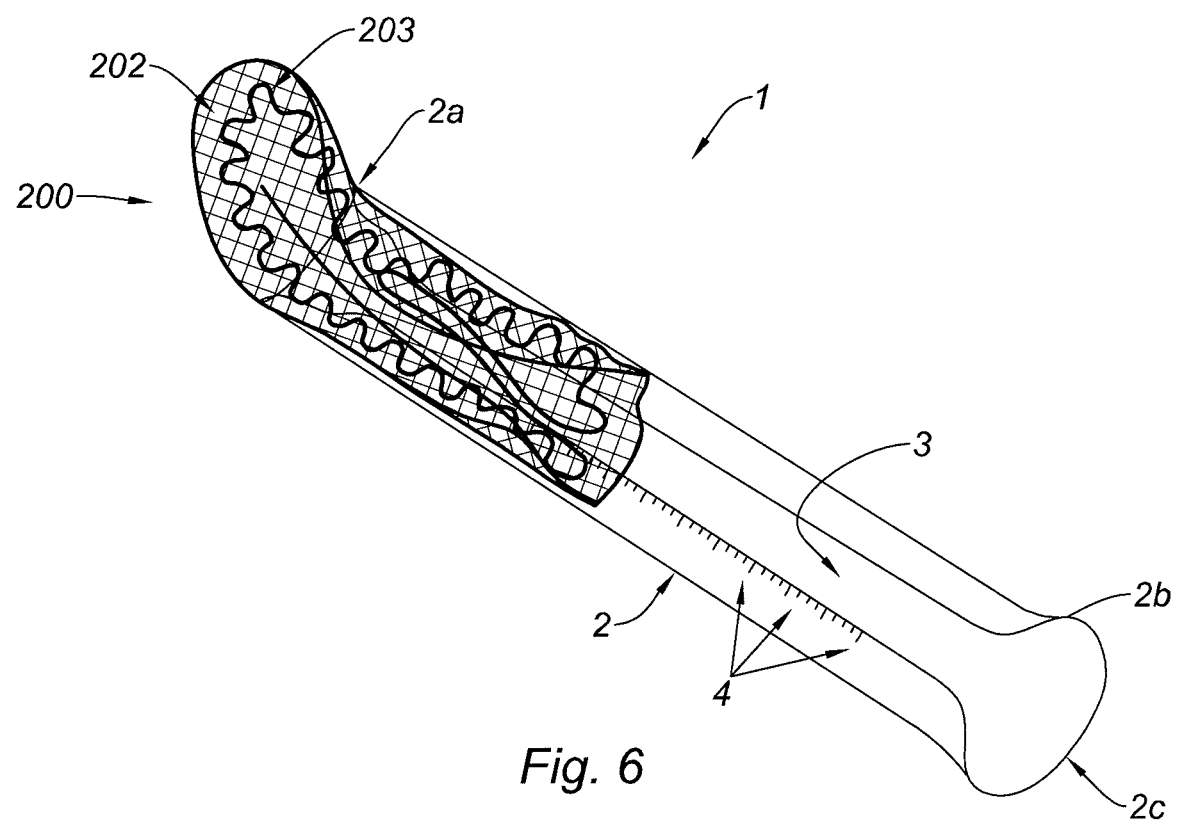

The present invention will emerge more clearly from the description given hereinafter and from the appended drawings, in which:

FIG. 1 is a representation in section of a median abdominal hernia or ventral rupture, FIG. 2 is a simplified view of the hernia from FIG. 1 after the surgeon has made an abdominal incision and removed the hernia sac, FIG. 3 is a top view of one embodiment of the device of the invention, FIG. 4 is a top view of an embodiment of a flexible prosthesis of the kit of the invention, FIG. 5 is a top view showing the step before introduction of another embodiment of a prosthesis of the kit of the invention in the device of FIG. 3, FIG. 6 is a top view of the folded prosthesis of FIG. 5 partially introduced in the device of the invention.

FIG. 1 represents a hernia defect 100 of the abdominal wall 101 that is characterized by a break in the continuity of the aponeurosis 102 surrounding the straight muscles 103 and a passage through the peritoneum 104 forming a sac, the hernia sac 105, that contains either fat (epiploon) or part of the viscera 106, and which then presses on the fatty tissues 107 and is flush with the skin 108. One treatment of a hernia defect 100 entails replacing and retaining the viscera 106 in the abdominal cavity 109.

FIG. 2 shows the hernia defect 100 from FIG. 1 after the surgeon has made an incision 110 in the skin 108, the abdominal wall 101 and the peritoneum 104 and has reduced the hernia sac. The viscera are not shown in FIG. 2: they have been pushed back into the abdominal cavity 109. The surgeon must now introduce into the abdominal cavity 109, via the incision 110 that has been made, a prosthesis for reinforcing the abdominal wall, before closing the incision 110 by means of sutures, for example. In the case of treatment of an umbilical or inguinal hernia by open surgery procedure, the size of the incision 110 is particularly small, for example of the order of 1 to 4 cm diameter.

With reference to FIG. 3 is shown an embodiment of a device 1 according to the invention. The device 1 of the invention is intended to be used for introducing a flexible prosthesis, such as the prosthesis 10 shown on FIG. 4, in a body incision such as the incision 110 of FIG. 2.

The device 1 comprises a globally tubular body 2 having a proximal end 2a and a distal end 2b. The tubular body 2 has an oblong cross section and is provided with an open longitudinal slit 3 extending from the proximal end 2a to the distal end 2b. Such a shape allows an easy introduction and movement of the folded prosthesis 10 inside the device 1.

The distal end 2b is further provided with a distal semi-tubular rounded extension 2c. On the example shown, the distal semi-tubular rounded extension 2c forms a single piece with the tubular body 2. In other embodiments, the distal semi-tubular rounded extension could be an added element and/or formed from another material than that of the tubular body 2. The distal semi-tubular rounded extension 2c is intended to be introduced first in the incision 110 of the body of the patient. Its distal rounded shape allows an easy introduction of the device 1 in an incision, even if the incision is of very small size, such as 3 or 4 cm long. In addition, the semi-tubular shape of the distal semi-tubular rounded extension 2c facilitates the ejection of the prosthesis from the device 1 at the time the prosthesis is delivered on the implantation site.

The distal semi-tubular rounded extension 2c may also be used for further dissection if the dissection pocket completed by the surgeon in the first place proves to be too small in the end.

The longitudinal slit 3 facilitates the sliding of the prosthesis inside the tubular body 2, from the proximal end 2a to the distal end 2b.

The proximal end 2a of the tubular body 2 is provided with a proximal semi-tubular extension 2d forming a partial funnel. On the example shown, the proximal semi-tubular rounded extension 2d forms a single piece with the tubular body 2. In other embodiments, the proximal semi-tubular rounded extension could be an added element and/or formed from another material than that of the tubular body 2. The partial funnel formed by the proximal semi-tubular extension 2d allows an easier introduction of the folded prosthesis in the tubular body. In addition, such a shape helps an automatic folding of the prosthesis into the tubular body, as the sloped walls of the proximal end of the tubular body naturally urge the material forming the prosthesis, for example a mesh, towards the inside of the tubular body.

With reference to FIG. 3, the device 1 is further provided with markings 4 distributed along the length of the tubular body 2. These markings define a ruler. Such a ruler may help the surgeon measuring the length of the dissection he has completed. In particular, the surgeon may thus determine whether he has dissected an adequately large enough pocket for the insertion of the prosthesis. The presence of a rule on the tubular body 2 is more accurate than the "finger" measurement system usually used by surgeons. The situation where the surgeon attempts to position the prosthesis at the implantation site only to discover that he has not dissected enough and that he must remove the prosthesis, dissect further and then re-introduce the prosthesis may therefore be avoided with the device 1 of the invention. The device of the invention may therefore allow saving time and avoiding potential irritation and infection.

The tubular body 2 may be made of any biocompatible material such as plastic material usually used in surgical applications. The tubular body 2 is preferably made of a transparent material. The surgeon is thus able to easily check the position of the folded prosthesis inside the tubular body 2, as well as the sliding and movement of the prosthesis from the proximal end of the tubular body to its distal end. He can then easily proceed to the ejection of the prosthesis at the implantation site.

The tubular body may be made from a material selected from poly(ethylene terephthalate) glycol (PETG), polyethylene terephthalate (PET), polypropylene, polycarbonate and mixtures thereof. These materials provide to the walls of the tubular body a smooth surface facilitating on one hand the sliding of the prosthesis inside the tubular body and easing on the other hand the introduction of the device in the incision.

With reference to FIG. 4 is shown a flexible prosthesis 10 suitable for being introduced into a small incision and transported to an implantation site in open surgery thanks to the device 1 of the invention of FIG. 3. For example, the prosthesis 10 is textile based. The prosthesis 10 may be formed of a mesh 11, of globally oval shape on the example shown. The prosthesis 10 is reinforced with a frame 12.

On the example shown, the mesh 11 may be made from a knitted, woven or non-woven arrangement of biocompatible threads. This mesh 11 is sufficiently flexible to be folded when the prosthesis is introduced into the abdominal cavity 109 via the incision 110. However, the mesh is generally a textile having no elasticity enabling it to return to a spread out configuration of its own accord after it has been folded up. Such meshes are well known to the person skilled in the art and are not described in more detail here. The mesh may be supplied in the form of a strip that is cut to the dimensions of the defect to be treated. In the example represented, the mesh 11 has an oval shape. In other embodiments, the mesh may be of rectangular or square shape, or any shape adapted to the defect to be treated.

On the example shown, the frame 12 substantially adopts the shape of the exterior peripheral edge of the mesh 11. The frame 12 is resilient, so as to allow the prosthesis 10 to move from a compact configuration, in which it is folded up on itself and in which it occupies a small volume, to a spread out configuration, as shown on FIG. 4, corresponding to the implantation configuration.

With reference to FIG. 5, is shown the step before introduction of another embodiment of a prosthesis 200 into the device of FIG. 3.

The prosthesis 200 comprises a biocompatible textile 202 and a reinforcing element in the form of a frame 203.

The textile 202 has a generally elongate shape, similar to an oval or egg shape, defining a longitudinal axis A and a transversal axis B. In an implanted configuration of the prosthesis 202 of FIG. 5, the longitudinal axis A is aligned on the medial-lateral axis of a human body and the transversal axis B is aligned on the cranial-caudal axis of a human body.

The textile 202 is thus delimited by a peripheral outer edge 204. The textile 202 comprises a medial end 202a, a lateral end 202b, a cranial part 202c and a caudal part 202d. The peripheral outer edge 204 is therefore formed of a convex medial edge 204a, a convex cranial edge 204c, a convex lateral edge 204b and a convex caudal edge 204d.

In the example shown, the textile 202 has the general shape of the section of an egg by a longitudinal plane. Such a shape is particularly suitable for the repair of an inguinal hernia. In particular, the cranial part 202c of the textile 202 is designed and shaped so as to efficiently cover the anterior muscle wall, the upper part of the os pubis and Cooper's ligament, while the caudal part 202d of the textile 202 is designed and shaped so as to cover efficiently the iliac vessels and spermatic vessels and part of the psoas muscle. In this view, the cranial part 202c is generally larger than the caudal part 202d. In addition, the medial end 202a has a rounded configuration that makes it capable of overlying and covering the orifice of the inguinal canal. The lateral end 202b has also a rounded configuration, but of smaller size than the medial end 202a, as it is located away from the orifice of the inguinal canal in an area where less foreign material is needed and desired.

In other embodiments, the textile 202 could have a globally oval or rectangular shape or could be protean if the shape in question is generally elongate and is adapted to cover the hernia defect in the inguinal region as explained above.

The textile 202 is made up of an arrangement of biocompatible filaments, such as a knit, a woven or a nonwoven. The textile 202 may be in the form of a mesh, that is to say it has openings for better tissue integration. For example, the textile 202 can be a two-dimensional or three-dimensional knit. Such textiles in the form of meshes or knits are well known to a person skilled in the art and are not described in any greater detail here.

The textile 202 can be bioresorbable, permanent or partially bioresorbable. As will become clear from the description below, the textile 202 is sufficiently flexible to be folded up, in particular at the time of introduction of the prosthesis into the device of the invention, along at least one folding direction. In general, however, the textile 202 does not have an inherent elasticity allowing it to spontaneously recover a spread-out configuration once it has been folded up. The textile 202 can be supplied in the form of a band, which one cuts to the dimensions of the defect to be treated.

The frame 203 acts as an element reinforcing the textile 202 in order to stiffen the latter and keep it in its generally elongate shape, as a tool for guiding the prosthesis 200 at the time of its introduction into the tubular body 2 of the device 1 of the invention, and as a tool for assisting in the deployment of the prosthesis 200 when the prosthesis 200 reaches the implantation site. For this purpose, the frame 203 is connected to the textile 202 and has an elasticity allowing it to be deformed under the effect of a temporary stress and allowing it to return to an initial state of rest once said stress has been removed.

The frame 203 is connected to the textile 202. It can be attached to the textile 202 by means of a seam, or else by means of an ultrasonic weld, by adhesive bonding, or by injection moulding.

In one embodiment, the frame 203 is connected to the textile 202 by injection moulding of one or more thermoplastic or thermosetting biocompatible materials. Such an embodiment makes it possible to secure the fixing of the frame to the textile in a particularly effective manner and to produce the prostheses according to the invention at an industrial scale.

In the injection moulding technique, a mould is formed in which, for example, there is a cavity defining a contour which corresponds to the contour of the frame that is to be obtained. The textile is held in an insert gate of the mould. The thermoplastic material used to produce the frame, for example a copolymer of polylactic acid and of polyglycolic acid, is heated and injected into the cavity using an injection moulding machine.

After the injection step, the mould is opened and the prosthesis 1 is withdrawn from the mould. Such a method allows the textile to be "embedded" in the part moulded over it. Thus, the frame 203, which is the overmoulded part, is connected to the textile, without any risk of its coming loose or fragmenting. The frame 203 is slightly set back from the peripheral convex outer edge 204.

Still with reference to FIG. 5, the frame 203 comprises a first segment which is a convex cranial segment 203c and which extends from the medial end 202a of the textile 202 to the lateral end 202b of the textile 202 substantially parallel to the convex cranial edge 204c. The frame 203 further comprises a second segment which is a caudal segment 203d substantially extending from the medial end 202a of the textile 202 to the lateral end 202b of the textile 202 and caudally spaced with respect to the convex cranial segment 203c. The frame 203 further comprises a lateral corner segment 203b joining together the convex cranial segment 203c and the caudal segment 203d in the region of the lateral end 202b of the textile 202.

Eventually, always with reference to FIG. 5, the frame 203 comprises a last segment which is a folding segment 205 configured for joining the medial end of the convex cranial segment 203c to the medial end of the caudal segment 203d. The frame 203 encompasses all these segments, convex cranial segment 203c, lateral corner segment 203b, caudal segment 203d and folding segment 205, in a continuous way. The frame 203 is therefore continuous. The shape of the frame 203 leaves the region of the medial end 202a of the textile 202 free of any frame structure. On the example shown, the folding segment 205 is a U shaped body 207 extending towards a center of the textile.

Thus, in the example shown in FIG. 5, the folding segment (205, 207) defines a sort of mouth of the frame 203 in the medial end 202a of the textile 202. The presence of this mouth allows an easy folding of the textile 202 and therefore of the prosthesis 200 when a pressure, such as the force F shown on FIG. 5 is exerted on the frame 203. This pressure allows reducing the volume occupied by the prosthesis 200 in the transversal direction.

In addition, because of the frame 203 being continuous, the step of pressing the prosthesis 200 together, by pressing the frame 203 together towards the longitudinal axis A of the prosthesis 200, does not create any projecting elements that could potentially perforate and damage the tissues. By virtue of its nature and its shape, the frame only has rounded and atraumatic outer contours.

In particular, the frame 203 has a structure, in other words a shape, and a nature, in other words a material, giving it an elasticity such that it is able to adopt a first, unstressed configuration in which the textile 202 and the prosthesis 200 are deployed and spread out as shown in FIG. 5, and a second, stressed configuration in which the frame 203 is subjected to a transversal force directed towards said longitudinal axis A and the convex cranial segment 203c, the caudal segment 203d and the folding segment 205 are substantially collected together and aligned on one folding direction, the textile 202 forming thereby at least one fold along the folding direction, as shown on FIG. 6.

As shown on FIG. 5, at least a part of the frame 203 has substantially the structure of a flat band forming undulations substantially in the plane of the textile 202. Such undulations allow a good conformability of the prosthesis. Such undulations further confer flexibility to the frame 203. In addition, such undulations confer a good resistance to folding to the prosthesis 200.

The caudal segment 203d may be concave. For example, the cranial part 202c is substantially planar and large enough so as to cover the anterior muscle wall, the orifice of the inguinal canal, the upper part of the os pubis and Cooper's ligament. The concavity of the caudal segment 203d confers to the caudal part 202d of the textile 202 an undulated and anatomical developed shape for matching the general shape of the lower inguinal structures, especially the spermatic and iliac vessels and the psoas muscle. The concavity of the caudal segment 203d gives the caudal part 2d a curved shape, this caudal part 202d thus forming with the cranial part 202c an angle corresponding to the angle formed by the parietal and vascular planes at the intersection thereof in the inguinal region of a human body. Thus, the cranial part 202c and the caudal part 202d are asymmetrical, which means that a left-hand prosthesis or right-hand prosthesis will be used depending on which side the hernia to be treated is located.

Still with reference to FIG. 5, the frame 203 further comprises a caudal extension 208 located on the caudal segment 203d and extending in the caudal direction substantially up to the caudal edge 204d of the textile 202. The caudal extension 208 helps deploying the caudal part 202d of the textile 202 once the prosthesis 200 is implanted. This caudal extension 208 helps spreading out the caudal part 202d of the textile on the biological tissues it is intended to cover, namely the iliac and spermatic vessels and part of the psoas muscle.

In order to proceed to the insertion of the prosthesis 200 into the device 1 of FIG. 5, the surgeon (not shown) folds the prosthesis 200 on itself by applying a pressure on the prosthesis 200 represented by the arrows F on FIG. 5. He then approaches the prosthesis 200 from the proximal end 2a of the device 1. Thanks to the proximal semi-tubular rounded extension 2d, the introduction of the prosthesis 200 inside the tubular device 1 is facilitated, as described above. The surgeon then pushes on the prosthesis 200 in the distal direction. The prosthesis 200 automatically follows the walls of the partial funnel formed by the proximal semi-tubular rounded extension 2d and it adopts a folded configuration within the tubular body 2, as shown on FIG. 6.

The surgeon then may introduce the distal end 2b of the device 1 inside the incision 110 (FIG. 2). As described above, this introduction is facilitated by the rounded shape of the distal semi-tubular extension 2c. The tubular body 2 then forms a barrier between the prosthesis 200 and the incision 110 edges. Thanks to the presence of the ruler, the surgeon can determine if has completed a long enough dissection. In addition, the device 1 of the invention allows standardizing the gesture of the surgeon, as the surgeon is ensured to introduce the distal end of the tubular body 2 at the right depth in the body of the patient, and therefore at the precise location of the implantation site.

When the surgeon has introduced the distal end of the device 1 at the right depth as described above, he pushes distally on the prosthesis 200 which slides easily inside the tubular body 2 thanks to the open longitudinal slit 3.

When the prosthesis 200 has substantially reached the distal end of the tubular body 2 and therefore the implantation site, the surgeon then ejects the prosthesis 200 from the device 1 by maintaining the prosthesis 200 fixed with respect to the body of the patient while he removes the device 1 by pulling said device 1 in the proximal direction. During this step, the surgeon may access directly to the prosthesis 200 with one of his hand thanks to the longitudinal slit 3 of the tubular body 2. The open shape of the distal end 2b of the tubular body, thanks to the presence of the distal semi-tubular extension 2c, allows the prosthesis 200 to start spreading out as it emerges from the tubular body 2 at the implantation site.

The device 1 of the invention therefore facilitates the introduction of a flexible prosthesis in an incision of very small size, such as for example an incision of 3 or 4 cm long, in open surgery procedure without necessitating the use of any dedicated ancillary device. The device of the invention may be of great help to the surgeon for dissecting a pocket of adequate size in the first place and therefore save time and potential infection.

The invention claimed is:

1. A device for introducing a flexible textile based prosthesis into a surgical incision, comprising a globally tubular body designed for receiving the prosthesis in a folded configuration in a sliding way and configured to form a barrier between the prosthesis and edges of the surgical incision, the tubular body having a proximal end provided with a proximal semi-tubular extension, a distal end provided with a distal semi-tubular rounded extension, a substantially oblong cross-section, and an open longitudinal slit extending from the proximal end to the distal end, wherein the tubular body includes markings defining a ruler along the open longitudinal slit.

2. The device according to claim 1, wherein the proximal semi-tubular extension and the tubular body are a single piece.

3. The device according to claim 1, wherein the proximal semi-tubular extension is an element added to the tubular body.

4. The device according to claim 1, wherein the distal semi-tubular rounded extension and the tubular body are a single piece.

5. The device according to claim 1, wherein the distal semi-tubular rounded extension is an element added to the tubular body.

6. The device according to claim 1, wherein the open longitudinal slit widens on the proximal semi-tubular extension and the distal semi-tubular rounded extension.

7. The device according to claim 1, wherein the proximal semi-tubular extension forms a partial funnel.

8. The device according to claim 7, wherein the proximal semi-tubular includes sloped walls configured to urge the prosthesis towards an inside of the tubular body.

9. The device according to claim 1, wherein walls of the tubular body are configured to compress via the open longitudinal slit reducing a cross-sectional area of the device.

10. The device according to claim 1, wherein the tubular body is made of a transparent material.

11. The device according to claim 1, wherein the tubular body is made from a material selected from poly(ethylene terephthalate) glycol (PETG), polyethylene terephthalate (PET), polypropylene, polycarbonate and mixtures thereof.

12. The device according to claim 1, wherein the tubular body is configured to allow direct access by a surgeon to the prosthesis via the open longitudinal slit while the device is removed from the surgical incision.

13. A method of conveying a flexible textile based prosthesis to an implantation site of an inguinal region during an open surgery procedure comprising:
inserting a folded prosthesis into a proximal end of a tubular body of a device for introducing the prosthesis to the implantation site, the tubular body having a substantially oblong cross-section and an open longitudinal slit extending from the proximal end to a distal end of the tubular body;
inserting the distal end of the tubular body into a surgical incision on abdominal skin and in a distal direction towards the site of implantation;
sliding the folded prosthesis through the tubular body towards the site of implantation; and
accessing the folded prosthesis via the open longitudinal slit to maintain the folded prosthesis in place while pulling the tubular body in a proximal direction away from the site of implantation removing the device from the surgical incision.

14. The method according to claim 13, wherein the distal end of the tubular body includes a distal semi-tubular rounded extension and the proximal end includes a proximal semi-tubular extension.

15. The method according to claim 14, wherein the open longitudinal slit widens on the proximal semi-tubular extension end and the distal semi-tubular rounded extension.

16. The method according to claim 13, wherein the tubular body includes markings defining a ruler along the open longitudinal slit.

17. The method according to claim 13, wherein the tubular body is made of a transparent material.

18. The method according to claim 13, wherein the tubular body is made from a material selected from poly (ethylene terephthalate) glycol (PETG), polyethylene terephthalate (PET), polypropylene, polycarbonate and mixtures thereof.

19. The method according to claim 13, wherein the surgical incision ranges from 3 to 4 cm in size.

20. The method according to claim 13, wherein the prosthesis includes an elongate shape having a medial end, a lateral end, a cranial part and a caudal part, the prosthesis being delimited by a peripheral outer edge formed of a convex medial edge, a convex cranial edge, a convex lateral edge and a caudal edge, and at least one reinforcing element in the form of a resilient frame connected to the textile and set back from the peripheral outer edge.

* * * * *